United States Patent
Bajwa et al.

(10) Patent No.: US 7,989,639 B2
(45) Date of Patent: Aug. 2, 2011

(54) PROCESS FOR MAKING SALTS OF N-HYDROXY-3-[4-[[[2-(2-METHYL-1H-INDOL-3-YL)ETHYL]AMINO]METHYL]PHENYL]-2E-2-PROPENAMIDE

(75) Inventors: Joginder S. Bajwa, Elmwood Park, NJ (US); David John Parker, West Milford, NJ (US); Joel Slade, Flanders, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/302,576

(22) PCT Filed: Jun. 7, 2007

(86) PCT No.: PCT/US2007/070562
§ 371 (c)(1),
(2), (4) Date: Nov. 26, 2008

(87) PCT Pub. No.: WO2007/146717
PCT Pub. Date: Dec. 21, 2007

(65) Prior Publication Data
US 2009/0187029 A1    Jul. 23, 2009

Related U.S. Application Data

(60) Provisional application No. 60/804,529, filed on Jun. 12, 2006, provisional application No. 60/853,259, filed on Oct. 20, 2006.

(51) Int. Cl.
*C07D 209/14* (2006.01)

(52) U.S. Cl. .................................................. 548/495
(58) Field of Classification Search .................. 548/495
See application file for complete search history.

(56) References Cited

FOREIGN PATENT DOCUMENTS

| GB | 776693 | 6/1957 |
|---|---|---|
| GB | 891413 | 3/1963 |
| GB | 2 185 020 | 7/1987 |
| WO | 02/22577 | 3/2002 |
| WO | 03/016307 | 2/2003 |
| WO | 03/039599 | 5/2003 |
| WO | 2005/105740 | 11/2005 |
| WO | WO 2006/021397 | 3/2006 |

OTHER PUBLICATIONS

Agharkar S et al: "Enhancement of Solubility of Drug Salts by Hydrophilic Counterions: Properties of Organic Salts of an Animalarial Drug" Journal of Pharmaceutical Sciences, American Pharmaceutical Association, Washington, US. vol. 65, No. 5 May 1976, pp. 747-749.
Search Report prepared by Austrian Patent Office dated Jul. 30, 2010 for Singapore Patent Application No. 200808475-8.

*Primary Examiner* — Shawquia E Young
(74) *Attorney, Agent, or Firm* — Matthew Mulkeen

(57) ABSTRACT

Salts of N-hydroxy-3-[4-[[[2-(2-methyl-1H-indol-3-yl)ethyl]amino]methyl]phenyl]-2E-2-propenamide are prepared by various methods.

6 Claims, No Drawings

… … …

PROCESS FOR MAKING SALTS OF N-HYDROXY-3-[4-[[[2-(2-METHYL-1H-INDOL-3-YL)ETHYL]AMINO]METHYL]PHENYL]-2E-2-PROPENAMIDE

This application claims benefit of U.S. Provisional Application No. 60/804,529, filed 12 Jun. 2006 and U.S. Provisional Application No. 60/853,259 filed 20 Oct. 2006, which in their entirety are herein incorporated by reference.

BACKGROUND OF THE INVENTION

1. Field of the Invention

This invention relates to processes for making salts of N-hydroxy-3-[4-[[[2-(2-methyl-1H-indol-3-yl)ethyl]amino]methyl]phenyl]-2E-2-propenamide.

2. Related Background Art

The compound N-hydroxy-3-[4-[[[2-(2-methyl-1H-indol-3-yl)ethyl]amino]methyl]phenyl]-2E-2-propenamide (alternatively, N-hydroxy-3-(4-{[2-(2-methyl-1H-indol-3-yl)-ethylamino]-methyl}-phenyl)-acrylamide) has the formula

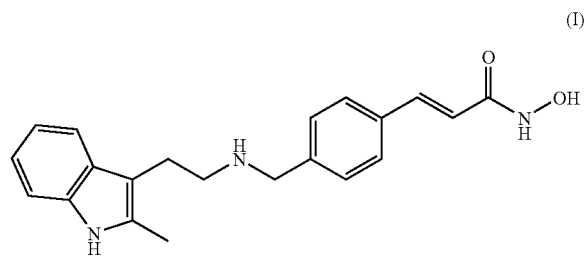

(I)

as described in WO 02/22577. Valuable pharmacological properties are attributed to this compound; thus, it can be used, for example, as a histone deacetylase inhibitor useful in therapy for diseases which respond to inhibition of histone deacetylase activity. WO 02/22577 does not disclose any specific salts or salt hydrates or solvates of N-hydroxy-3-[4-[[[2-(2-methyl-1H-indol-3-yl)ethyl]amino]methyl]phenyl]-2E-2-propenamide.

SUMMARY OF THE INVENTION

The present invention is directed to a method of preparing a crystalline salt of N-hydroxy-3-[4-[[[2-(2-methyl-1H-indol-3-yl) ethyl]amino]methyl]phenyl]-2E-2-propenamide comprising the steps of: (a) dissolving or suspending N-hydroxy-3-[4-[[[2-(2-methyl-1H-indol-3-yl)ethyl]amino]methyl]phenyl]-2E-2-propenamide free base in an appropriate amount of solvent; and (b) treating the N-hydroxy-3-[4-[[[2-(2-methyl-1H-indol-3-yl)ethyl]amino]methyl]phenyl]-2E-2-propenamide free base at an appropriate temperature with a salt forming agent, wherein the salt forming agent is selected from the group consisting of suppliers of hydrochloride, lactate, maleate, mesylate, tartarate, acetate, benzoate, citrate, fumarate, gentisate, malate, malonate, oxalate, phosphate, propionate, sulfate, succinate, sodium, potassium, calcium or zinc ions.

The present invention is further directed to a method of preparing the hydrochloride salt of N-hydroxy-3-[4-[[[2-(2-methyl-1H-indol-3-yl)ethyl]amino]methyl]phenyl]-2E-2-propenamide comprising the steps of: (a) suspending N-hydroxy-3-[4-[[[2-(2-methyl-1H-indol-3-yl)ethyl]amino]methyl]phenyl]-2E-2-propenamide free base monohydrate in ethanol; (b) adding hydrochloric acid dropwise with stirring at ambient temperature, wherein the hydrochloric acid is present in a 50% molar excess amount; (c) stirring the reaction mixture for a time sufficient to cause precipitation of the hydrochloride salt; and (d) cooling the reaction mixture; and optionally (e) isolating the precipitated hydrochloride salt of N-hydroxy-3-[4-[[[2-(2-methyl-1H-indol-3-yl)ethyl]amino]methyl]phenyl]-2E-2-propenamide; (f) washing the salt with cold ethanol; and (g) drying the salt.

The present invention is further directed to a method of preparing the 1-tartarate salt of N-hydroxy-3-[4-[[[2-(2-methyl-1H-indol-3-yl)ethyl]amino]methyl]phenyl]-2E-2-propenamide comprising the steps of: (a) suspending N-hydroxy-3-[4-[[[2-(2-methyl-1H-indol-3-yl)ethyl]amino]methyl]phenyl]-2E-2-propenamide free base monohydrate in ethanol; (b) adding 1-tartaric acid dropwise with stirring at 60° C., wherein the 1-tartaric acid is present in a 10% molar excess amount; (c) stirring the reaction mixture for a time sufficient to cause precipitation of the 1-tartarate salt; and (d) cooling the reaction mixture; and optionally (e) isolating the precipitated 1-tartarate salt of N-hydroxy-3-[4-[[[2-(2-methyl-1H-indol-3-yl)ethyl]amino]methyl]phenyl]-2E-2-propenamide; (f) washing the salt with cold ethanol; and (g) drying the salt.

The present invention is further directed to a method of preparing the lactate monohydrate salt of N-hydroxy-3-[4-[[[2-(2-methyl-1H-indol-3-yl)ethyl]amino]methyl]phenyl]-2E-2-propenamide comprising the steps of: (a) suspending N-hydroxy-3-[4-[[[2-(2-methyl-1H-indol-3-yl)ethyl]amino]methyl]phenyl]-2E-2-propenamide free base monohydrate in acetone; (b) adding lactic acid dropwise with stirring at ambient temperature, wherein the lactic acid is present in an equimolar amount; (c) stirring the reaction mixture for a time sufficient to cause precipitation of the lactate monohydrate salt; and (d) cooling the reaction mixture; and optionally (e) isolating the precipitated lactate monohydrate salt of N-hydroxy-3-[4-[[[2-(2-methyl-1H-indol-3-yl) ethyl]amino]methyl]phenyl]-2E-2-propenamide; (f) washing the salt with cold acetone; and (g) drying the salt.

The present invention is further directed to a method of preparing the anhydrous lactate salt of N-hydroxy-3-[4-[[[2-(2-methyl-1H-indol-3-yl) ethyl]amino]methyl]phenyl]-2E-2-propenamide comprising the steps of: (a) providing a solution of lactic acid; (b) suspending N-hydroxy-3-[4-[[[2-(2-methyl-1H-indol-3-yl) ethyl]amino]methyl]phenyl]-2E-2-propenamide free base in water; (c) heating the suspension to an appropriate temperature; (d) adding the solution of lactic acid to form a solution: (e) seeding the solution with a suspension of the anhydrous lactate salt of N-hydroxy-3-[4-[[[2-(2-methyl-1H-indol-3-yl) ethyl]amino]methyl]phenyl]-2E-2-propenamide; (f) stirring the solution for a time; (g) heating the solution to a second appropriate temperature; (h) stirring the solution for a time; (i) cooling the solution; and (j) stirring the solution for a time sufficient to precipitate the anhydrous lactate salt of N-hydroxy-3-[4-[[[2-(2-methyl-1H-indol-3-yl) ethyl]amino]methyl]phenyl]-2E-2-propenamide; and optionally (k) isolating the precipitated anhydrous lactate salt of N-hydroxy-3-[4-[[[2-(2-methyl-1H-indol-3-yl)ethyl]amino]methyl]phenyl]-2E-2-propenamide; (l) washing the salt with water; and (m) drying the salt.

This invention is further directed to a method of preparing the anhydrous lactate salt of N-hydroxy-3-[4-[[[2-(2-methyl-1H-indol-3-yl) ethyl]amino]methyl]phenyl]-2E-2-propenamide comprising the steps of: (a) providing a solution of lactic acid; (b) suspending N-hydroxy-3-[4-[[[2-(2-methyl-1H-indol-3-yl) ethyl]amino]methyl]phenyl]-2E-2-propenamide free base in a 1:1 mixture of ethanol and water; (c) heating the suspension to an appropriate temperature; (d) adding the solution of lactic acid to form a solution; (e) cooling the solution; (f) seeding the solution with anhydrous lactate salt of N-hydroxy-3-[4-[[[2-(2-methyl-1H-indol-3-yl) ethyl]amino]methyl]phenyl]-2E-2-propenamide; (g) stirring the solution for a time; (h) cooling the solution; and (i) stirring the solution for a time sufficient to precipitate the anhydrous lactate salt of N-hydroxy-3-[4-[[[2-(2-methyl-1H-indol-3-yl) ethyl]amino]methyl]phenyl]-2E-2-propenamide; and optionally (j) isolating the precipitated anhydrous lactate salt of N-hydroxy-3-[4-[[[2-(2-methyl-1H-indol-3-yl)ethyl]amino]methyl]phenyl]-2E-2-propenamide; (k) washing the salt with water; and (l) drying the salt.

The present invention is further directed to a method of preparing the mesylate salt of N-hydroxy-3-[4-[[[2-(2-methyl-1H-indol-3-yl)ethyl]amino]methyl]phenyl]-2E-2-propenamide comprising the steps of: (a) suspending N-hydroxy-3-[4-[[[2-(2-methyl-1H-indol-3-yl)ethyl]amino]methyl]phenyl]-2E-2-propenamide free base monohydrate in ethyl acetate; (b) adding methanesulfonic acid dropwise with stirring at ambient temperature, wherein the methanesulfonic acid is present in an equimolar amount, to produce a precipitate; (c) heating the reaction mixture to a temperature ranging from about 40° C. to about 50° C. for a time ranging from about 2 to about 4 hours; and (d) cooling the reaction mixture to precipitate the mesylate salt; and optionally (e) isolating the precipitated mesylate salt of N-hydroxy-3-[4-[[[2-(2-methyl-1H-indol-3-yl) ethyl]amino]methyl]phenyl]-2E-2-propenamide; (f) washing the salt with cold ethyl acetate; and (g) drying the salt.

The present invention is further directed to a method of preparing the maleate salt of N-hydroxy-3-[4-[[[2-(2-methyl-1H-indol-3-yl)ethyl]amino]methyl]phenyl]-2E-2-propenamide comprising the steps of: (a) suspending N-hydroxy-3-[4-[[[2-(2-methyl-1H-indol-3-yl)ethyl]amino]methyl]phenyl]-2E-2-propenamide free base monohydrate in acetone; (b) adding maleic acid dropwise with stirring at 45° C., wherein the maleic acid is present in an equimolar amount; (c) stirring the reaction mixture for a time sufficient to cause precipitation of the maleate salt; and (d) cooling the reaction mixture; and optionally (e) isolating the precipitated maleate salt of N-hydroxy-3-[4-[[[2-(2-methyl-1H-indol-3-yl)ethyl]amino]methyl]phenyl]-2E-2-propenamide; (f) washing the salt with cold acetone; and (g) drying the salt.

DETAILED DESCRIPTION OF THE INVENTION

As used herein, "salt" refers to a compound prepared by the reaction of an organic acid or base drug with a pharmaceutically acceptable mineral or organic acid or base; as used herein, "salt" includes hydrates and solvates of salts made in accordance with this invention. Exemplary pharmaceutically acceptable mineral or organic acids or bases are as listed in Tables 1-8 in *Handbook of Pharmaceutical Salts*, P. H. Stahl and C. G. Wermuth (eds.), VHCA, Zurich 2002, pp. 334-345. Co-pending U.S. patent application Ser. No. 12/302,571, filed concurrently herewith, addresses the actual salts of N-hydroxy-3-[4-[[[2-(2-methyl-1H-indol-3-yl)ethyl]amino]methyl]phenyl]-2E-2-propenamide; the disclosure of that co-pending application is incorporated in its entirety by reference herein. As used herein, "polymorph" refers to a distinct "crystal modification" or "polymorphic form" or "crystalline form", which differs from another with respect to x-ray powder diffraction pattern, physicochemical and/or pharmacokinetic properties, and thermodynamic stability. Co-pending U.S. patent application Ser. No. 12/302,564, filed concurrently herewith, addresses the various polymorphic forms of N-hydroxy-3-[4-[[[2-(2-methyl-1H-indol-3-yl)ethyl]amino]methyl]phenyl]-2E-2-propenamide and salts thereof; the disclosure of that co-pending application is incorporated in its entirety by reference herein.

The first embodiment of the present invention is directed to a method of preparing a crystalline salt of N-hydroxy-3-[4-[[[2-(2-methyl-1H-indol-3-yl)ethyl]amino]methyl]phenyl]-2E-2-propenamide comprising the steps of (a) dissolving or suspending N-hydroxy-3-[4-[[[2-(2-methyl-1H-indol-3-yl)ethyl]amino]methyl]phenyl]-2E-2-propenamide free base in an appropriate amount of solvent; and (b) treating the N-hydroxy-3-[4-[[[2-(2-methyl-1H-indol-3-yl) ethyl]amino]methyl]phenyl]-2E-2-propenamide free base at an appropriate temperature with a salt forming agent, wherein the salt forming agent is selected from the group consisting of suppliers of hydrochloride, lactate, maleate, mesylate, tartarate, acetate, benzoate, citrate, fumarate, gentisate, malate, malonate, oxalate, phosphate, propionate, sulfate, succinate, sodium, potassium, calcium or zinc ions.

In the first step of the inventive method, N-hydroxy-3-[4-[[[2-(2-methyl-1H-indol-3-yl)ethyl]amino]methyl]phenyl]-2E-2-propenamide free base is dissolved or suspended in an appropriate amount of solvent at an appropriate temperature. N-hydroxy-3-[4-[[[2-(2-methyl-1H-indol-3-yl)ethyl]amino]methyl]phenyl]-2E-2-propenamide free base suitable for use in the present invention can take any hydrate, solvate or polymorphic form. In a preferred embodiment of the present invention, N-hydroxy-3-[4-[[[2-(2-methyl-1H-indol-3-yl)ethyl]amino]methyl]phenyl]-2E-2-propenamide free base monohydrate form $H_A$ is employed.

Solvents suitable for use in the present invention include, without limitation, ethanol, isopropyl alcohol, acetone, ethyl acetate, ethanol/water mixture, isopropyl alcohol/water mixture, acetone/water mixture, acetonitrile, tetrahydrofuran, 2-propanol and mixtures thereof.

In the second step of the present inventive method, the N-hydroxy-3-[4-[[[2-(2-methyl-1H-indol-3-yl) ethyl]amino]methyl]phenyl]-2E-2-propenamide free base is treated at an appropriate temperature with an appropriate salt forming agent selected from suppliers of hydrochloride, lactate, maleate, mesylate, tartarate, acetate, benzoate, citrate, fumarate, gentisate, malate, malonate, oxalate, phosphate, propionate, sulfate, succinate, sodium, potassium, calcium or zinc ions. The appropriate temperature typically ranges from about 0° C. to about 60° C., more preferably from about ambient temperature to about 60° C. Most of the potential salt forming agents are capable of forming a salt at ambient temperature; suppliers for citrate, tartarate and propionate required elevated temperature for salt formation.

Suitable suppliers of hydrochloride, lactate, maleate, mesylate, tartarate, acetate, benzoate, citrate, fumarate, gentisate, malate, malonate, oxalate, phosphate, propionate, sulfate, succinate, sodium, potassium, calcium or zinc ions include corresponding acids, i.e., hydrochloric acid, lactic acid, maleic acid, methanesulfonic acid, tartaric acid, acetic acid, benzoic acid, citric acid, fumaric acid, gentisic acid, malic acid, malonic acid, oxalic acid, phosphoric acid, propionic acid, sulfuric acid, succinic acid, NaOH, KOH, $CaCl_2$, and $ZnCl_2$. Suitable suppliers include, without limitation, those listed above, as well as variously substituted counterparts of those listed above. One of ordinary skill in the art will readily understand that the suitable suppliers are the salt forming agents used in the methods of this invention.

Typically the salt forming agent is provided in an equimolar amount as compared with the amount of N-hydroxy-3-[4-[[[2-(2-methyl-1H-indol-3-yl)ethyl]amino]methyl]phenyl]-2E-2-propenamide used. In other embodiments of the invention, the salt forming agent can be provided in an excess, i.e., in a molar ratio of N-hydroxy-3-[4-[[[2-(2-methyl-1H- indol-3-yl)ethyl]amino]methyl]phenyl]-2E-2-propenamide to salt forming agent ranging from about 1:1 to about 1:2.

In optional steps of the present inventive method, the temperature of the mixture of N-hydroxy-3-[4-[[[2-(2-methyl-1H-indol-3-yl)ethyl]amino]methyl]phenyl]-2E-2-propenamide and salt forming agent is lowered, the salt is isolated by filtration or some other suitable means and the isolated salt is dried to remove residual solvent. For example, where the mixture of N-hydroxy-3-[4-[[[2-(2-methyl-1H-indol-3-yl)ethyl]amino]methyl]phenyl]-2E-2-propenamide and salt forming agent affords a clear solution, it has been found helpful to lower the temperature to about 4° C. in order to produce a precipitate.

It is important to note that variation of the parameters of the present inventive method results in the achievement of various polymorphic forms of the salts of N-hydroxy-3-[4-[[[2-(2-methyl-1H-indol-3-yl)ethyl]amino]methyl]phenyl]-2E-2-propenamide. This is made clear in the below-presented examples and in co-pending U.S. patent application Ser. No. 12/302,572.

A preferred embodiment of the present invention is directed to a method of preparing the hydrochloride salt of N-hydroxy-3-[4-[[[2-(2-methyl-1H-indol-3-yl)ethyl]amino]methyl]phenyl]-2E-2-propenamide comprising the steps of: (a) suspending N-hydroxy-3-[4-[[[2-(2-methyl-1H-indol-3-yl)ethyl]amino]methyl]phenyl]-2E-2-propenamide free base monohydrate in ethanol; (b) adding hydrochloric acid dropwise with stirring at ambient temperature, wherein the hydrochloric acid is present in a 50% molar excess amount; (c) stirring the reaction mixture for a time sufficient to cause precipitation of the hydrochloride salt; and (d) cooling the reaction mixture. Optional steps for this embodiment of the invention include (e) isolating the precipitated hydrochloride salt of N-hydroxy-3-[4-[[[2-(2-methyl-1H-indol-3-yl)ethyl]amino]methyl]phenyl]-2E-2-propenamide; (f) washing the salt with cold ethanol; and (g) drying the salt.

Another preferred embodiment of the present invention is directed to a method of preparing the l-tartarate salt of N-hydroxy-3-[4-[[[2-(2-methyl-1H-indol-3-yl)ethyl]amino]methyl]phenyl]-2E-2-propenamide comprising the steps of: (a) suspending N-hydroxy-3-[4-[[[2-(2-methyl-1H-indol-3-yl)ethyl]amino]methyl]phenyl]-2E-2-propenamide free base monohydrate in ethanol; (b) adding l-tartaric acid dropwise with stirring at 60° C., wherein the l-tartaric acid is present in a 10% molar excess amount; (c) stirring the reaction mixture for a time sufficient to cause precipitation of the l-tartarate salt; and (d) cooling the reaction mixture. Optional steps for this embodiment include (e) isolating the precipitated l-tartarate salt of N-hydroxy-3-[4-[[[2-(2-methyl-1H-indol-3-yl)ethyl]amino]methyl]phenyl]-2E-2-propenamide; (f) washing the salt with cold ethanol; and (g) drying the salt.

Yet another preferred embodiment of the present invention is directed to a method of preparing the lactate monohydrate salt of N-hydroxy-3-[4-[[[2-(2-methyl-1H-indol-3-yl)ethyl]amino]methyl]phenyl]-2E-2-propenamide comprising the steps of: (a) suspending N-hydroxy-3-[4-[[[2-(2-methyl-1H-indol-3-yl)ethyl]amino]methyl]phenyl]-2E-2-propenamide free base monohydrate in acetone; (b) adding lactic acid dropwise with stirring at ambient temperatures wherein the lactic acid is present in an equimolar amount; (c) stirring the reaction mixture for a time sufficient to cause precipitation of the lactate monohydrate salt; and (d) cooling the reaction mixture. Optional steps for this embodiment include (e) isolating the precipitated lactate monohydrate salt of N-hydroxy-3-[4-[[[2-(2-methyl-1H-indol-3-yl)ethyl]amino]methyl]phenyl]-2E-2-propenamide; (f) washing the salt with cold acetone; and (g) drying the salt.

Still another preferred embodiment of the present invention is directed to a method of preparing the anhydrous lactate salt of N-hydroxy-3-[4-[[[2-(2-methyl-1H-indol-3-yl) ethyl]amino]methyl]phenyl]-2E-2-propenamide comprising the steps of: (a) providing a solution of lactic acid; (b) suspending N-hydroxy-3-[4-[[[2-(2-methyl-1H-indol-3-yl)ethyl]amino]methyl]phenyl]-2E-2-propenamide free base in water; (c) heating the suspension to an appropriate temperature such as about 48° C.; (d) adding the solution of lactic acid to form a solution; (e) seeding the solution with a suspension of the anhydrous lactate salt of N-hydroxy-3-[4-[[[2-(2-methyl-1H-indol-3-yl)ethyl]amino]methyl]phenyl]-2E-2-propenamide; (f) stirring the solution for a time; (g) heating the solution to a second appropriate temperature; (h) stirring the solution for a time; (i) cooling the solution; and (j) stirring the solution for a time sufficient to precipitate the anhydrous lactate salt of N-hydroxy-3-[4-[[[2-(2-methyl-1H-indol-3-yl)ethyl]amino]methyl]phenyl]-2E-2-propenamide. Preferably lactic acid is provided in an amount ranging from about 1.1 molar equivalent to about 1.3 molar equivalent with respect to the free base. Preferably the lactic acid solution is added slowly over a period of time such as over 30 minutes. Preferably crystallization takes place at a temperature ranging from about 15° C. to about 50° C. Optional steps for this embodiment include (k) isolating the precipitated anhydrous lactate salt of N-hydroxy-3-[4-[[[2-(2-methyl-1H-indol-3-yl)ethyl]amino]methyl]phenyl]-2E-2-propenamide; (l) washing the salt with water; and (m) drying the salt. Drying is preferably conducted in vacuo at a temperature of about 50° C. In a preferred embodiment, step (a) is accomplished by diluting DL-lactic acid in water, heating to a temperature of about 90° C. for a period of time of about 15 hours and then cooling.

Still another preferred embodiment of the present invention is directed to an alternative method of preparing the anhydrous lactate salt of N-hydroxy-3-[4-[[[2-(2-methyl-1H-indol-3-yl)ethyl]amino]methyl]phenyl]-2E-2-propenamide comprising the steps of: (a) providing a solution of lactic acid; (b) suspending N-hydroxy-3-[4-[[[2-(2-methyl-1H-indol-3-yl)ethyl]amino]methyl]phenyl]-2E-2-propenamide free base in a 1:1 mixture of ethanol and water; (c) heating the suspension to an appropriate temperature such as about 60° C.; (d) adding the solution of lactic acid to form a solution; (e) cooling the solution; (f) seeding the solution with anhydrous lactate salt of N-hydroxy-3-[4-[[[2-(2-methyl-1H-indol-3-yl) ethyl]amino]methyl]phenyl]-2E-2-propenamide; (g) stirring the solution for a time; (h) cooling the solution; and (i) stirring the solution for a time sufficient to precipitate the anhydrous lactate salt of N-hydroxy-3-[4-[[[2-(2-methyl-1H-indol-3-yl) ethyl]amino]methyl]phenyl]-2E-2-propenamide. Preferably the lactic acid solution is added slowly over a period of time such as over 30 minutes. Optional steps for this embodiment include (j) isolating the precipitated anhydrous lactate salt of N-hydroxy-3-[4-[[[2-(2-methyl-1H-indol-3-yl)ethyl]amino]methyl]phenyl]-2E-2-propenamide; (k) washing the salt with water; and (l) drying the salt. Drying is preferably conducted in vacuo at a temperature of about 45° C. In a preferred embodiment, step (a) is accomplished by diluting DL-lactic acid in water, heating to a temperature of about 90° C. for a period of time of about 15 hours and then cooling.

Still another preferred embodiment of the present invention is directed to a method of preparing the mesylate salt of N-hydroxy-3-[4-[[[2-(2-methyl-1H-indol-3-yl)ethyl]amino]methyl]phenyl]-2E-2-propenamide comprising the steps of: (a) suspending N-hydroxy-3-[4-[[[2-(2-methyl-1H-indol-3-yl)ethyl]amino]methyl]phenyl]-2E-2-propenamide free base monohydrate in ethyl acetate; (b) adding methanesulfonic acid dropwise with stirring at ambient temperature, wherein the methanesulfonic acid is present in an equimolar amount, to produce a precipitate; (c) heating the reaction mixture to a temperature ranging from about 40° C. to about 50° C. for a time ranging from about 2 to about 4 hours; and (d) cooling the reaction mixture. Optional steps for this embodiment include (e) isolating the precipitated mesylate salt of N-hydroxy-3-[4-[[[2-(2-methyl-1H-indol-3-yl) ethyl]amino]methyl]phenyl]-2E-2-propenamide; (f) washing the salt with cold ethyl acetate; and (g) drying the salt. It is noted that a yellow powder is initially formed in step (b); the yellow powder is a polymorph of the mesylate salt that contains more than the equimolar amount of methanesulfonic acid. As a result, this solid is very highly hygroscopic. However, upon gentle heating in step (c), the yellow powder is converted to a white crystalline solid that contains an equimolar amount of the methanesulfonic acid. This salt is non-hygroscopic. It is important to add the methanesulfonic acid at ambient temperature and to then increase the temperature; addition of the methanesulfonic acid at a higher temperature afforded immediate precipitation of the salt as a soft and gummy material.

Yet another preferred embodiment of the present invention is directed to a method of preparing the maleate salt of N-hydroxy-3-[4-[[[2-(2-methyl-1H-indol-3-yl) ethyl]amino]methyl]phenyl]-2E-2-propenamide comprising the steps of: (a) suspending N-hydroxy-3-[4-[[[2-(2-methyl-1H-indol-3-yl) ethyl]amino]methyl]phenyl]-2E-2-propenamide free base monohydrate in acetone; (b) adding maleic acid dropwise with stirring at 45° C., wherein the maleic acid is present in an equimolar amount; (c) stirring the reaction mixture for a time sufficient to cause precipitation of the maleate salt; and (d) cooling the reaction mixture. Optional steps for this embodiment include (e) isolating the precipitated maleate salt of N-hydroxy-3-[4-[[[2-(2-methyl-1H-indol-3-yl)ethyl]amino]methyl]phenyl]-2E-2-propenamide; (f) washing the salt with cold acetone; and (g) drying the salt.

Specific embodiments of the invention will now be demonstrated by reference to the following examples. It should be understood that these examples are disclosed solely by way of illustrating the invention and should not be taken in any way to limit the scope of the present invention.

In the following examples, with regard to crystallinity, "excellent" refers to a material having XRPD main peaks which are sharp and have intensities above 70 counts; "good" refers to a material having XRPD main peaks which are sharp and have intensities within 30-70 counts; and "poor" refers to a material having XRPD main peaks which are broad and have intensities below 30 counts. In addition, "loss on drying" (LOD) refers to weight loss determined between ambient and decomposition temperatures. The later is approximated by the onset of the first derivative of the thermogravimetric curve vs. temperature. This is not the true onset, since weight loss does not occur with the same rate for all the salts. Hence, the actual decomposition temperature may be lower than that stated. Salt formation, stoichiometry, and the presence or absence of solvents is confirmed by observing the $^1$H-NMR chemical shifts of the corresponding salt forming agents and reaction solvents (the tables contain one characteristic chemical shift for salt forming agents or solvents). Water content could not be extracted from the NMR data, because the water peaks were broad. The extent of protonation of the free base is assessed by the change in the chemical shift of the benzylic ($H_{bz}$) protons. Further, salts of the present invention precipitated out as free-flowing powders (FFP), sticky amorphous materials (SAM) (which had a gummy consistency that tended to agglomerate, forming a single spherical mass or stick to the walls of the reaction vessel) or amorphous gels (AG). Finally, "-" indicates a measurement not taken.

EXAMPLE 1

Preparation of Acetate Salt

About 40 to 50 mg of N-hydroxy-3-[4-[[[2-(2-methyl-1H-indol-3-yl)ethyl]amino]methyl]phenyl]-2E-2-propenamide free base monohydrate was suspended in 1 ml of a solvent as listed in Table 1. A stoichiometric amount of acetic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 1

| Solvent | T, ° C. | Physical Appear. | Crystallinity and Form | LOD, % $T_{decomposition}$ ($T_{desolvation}$) | $^1$H-NMR |
|---|---|---|---|---|---|
| Acetone | ambient | FFP | Excellent $S_A$ | 13.5 (107.9) 147.9 | 1.89 (acetate, 3H) 2.08 (acetone, 6H) 3.74 ($H_{bz}$) |
| IPA | 60 | FFP | Good A | ~10.5 (72.5) 148.7 | — |
| AcOEt | 60 | FFP | Good A | 9.3 (105.1) 147.9 | 1.89 (acetate, 3H) 3.73 ($H_{bz}$) |

The salt forming reaction in acetone produced a highly crystalline salt, with the ratio of N-hydroxy-3-[4-[[[2-(2-methyl-1H-indol-3-yl)ethyl]amino]methyl]phenyl]-2E-2-propenamide to acetate of 1:1, identified as a stoichiometric acetone solvate $S_A$. The salt forming reaction in isopropyl alcohol and ethyl acetate at 60° C. produced the same crystalline, non-solvated acetate salt (form A). The accompanied weight loss above 105° C. is either due to the loss of water (if the salt is a hydrate) or loss of acetic acid or both.

EXAMPLE 2

Preparation of Benzoate Salt

About 40 to 50 mg of N-hydroxy-3-[4-[[[2-(2-methyl-1H-indol-3-yl)ethyl]amino]methyl]phenyl]-2E-2-propenamide free base monohydrate was suspended in 1 ml of a solvent as listed in Table 2. A stoichiometric amount of benzoic acid was subsequently added to the suspension. The mixture was stirred at ambient temperature (where a clear solution formed, stirring continued at 4° C.). Solids were collected by filtration and analyzed by XRPD, TGA and in some instances $^1$H-NMR.

TABLE 2

| Solvent | T/° C. | Physical Appear. | Crystallinity and Form | LOD % $T_{decomposition}$ | $^1$H-NMR |
|---|---|---|---|---|---|
| EtOH:H$_2$O (1:0.05) | ambient | FFP | excellent $S_A$ | 1.5 prior to dec. at 110° C. | — |
| IPA:H$_2$O (1:0.05) | ambient | FFP | excellent $S_B$ | 6.3* (isothermal at 120° C.) | 1.02 (IPA, 6H) 3.83 (H$_{bz}$) |
| EtOH | ambient | FFP | excellent $S_A$ | 5.2* (isothermal at 120° C.) | 1.04 (EtOH, 5H) 3.43 (EtOH, 1H) 7.93 (benzoate, 2H) 3.85 (H$_{bz}$) |
| IPA | ambient | FFP | Excellent $S_B$ | 1.5% prior dec. at 100° C. | — |
| Acetone | ambient | FFP | Excellent A | 0.5% 160.2 | 7.93 (benzoate, 2H) 3.84 (H$_{bz}$) |

*Isothermal hold at 120° C. for 10 minutes

The salt forming reaction in ethanol alone and with water produced the same ethanol solvate S$_A$. The stoichiometry of the protonated base:benzoate:ethanol is 1:1:0.5 by NMR. Solvent loss and decomposition are closely spaced events at the heating rate of 10° C./min, and the ethanol content could not be determined initially. Eventually, it was determined by holding at 120° C. for 10 min. The LOD of 5.2% corresponds to 0.5 moles of ethanol per formula unit. Isopropyl alcohol alone and with water produced the same isopropanol (IPA) solvate SB. The stoichiometry of the protonated base:benzoate is 1:1 by NMR. Solvent loss and decomposition are closely spaced at the heating rate of 10° C./min, and the isopropanol content could not be determined initially. Eventually, it was determined by holding at 120° C. for 10 min. The 6.3% LOD corresponds to 0.5 moles of IPA per formula unit. Based on solvent content and XRPD patterns, the two solvates SA and SB appeared to be isostructural. The salt forming reaction in acetone produced benzoate salt that did not contain any solvent or water, a 1:1 stoichiometric salt of excellent crystallinity and high decomposition temperature (form A).

EXAMPLE 3

Formation of Hydrochloride Salt

About 40 to 50 mg of N-hydroxy-3-[4-[[[2-(2-methyl-1H-indol-3-yl)ethyl]amino]methyl]phenyl]-2E-2-propenamide free base was suspended in 1 ml of a solvent as listed in Table 3. A stoichiometric amount of hydrochloric acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 3

| Solvent | T, ° C. | Physical Appear. | Crystallinity and Form | LOD, % $T_{decomposit.}$ | $^1$H-NMR |
|---|---|---|---|---|---|
| EtOH:H$_2$O (1:0.05) | 60 | Clear solut. to FFP | Excellent A | 0.5 | 4.20 (H$_{bz}$) |
| EtOH | Ambient | Clear solut. to FFP | excellent A | 1.1 232.3 | 4.19 (H$_{bz}$) |
| IPA | Ambient | FFP yellow to white powder | excellent A | — | 418 (H$_{bz}$) |
| Acetone | Ambient | FFP to SAM to FFP | excellent A | — | 4.18 (H$_{bz}$) |
| AcOEt | Ambient | FFP to SAM to FFP | excellent A | — | — |

All the above five reactions produced the same crystalline salt. The salt was anhydrous and decomposed at high temperature.

EXAMPLE 4

Formation of Hemi-Citrate Salt

About 40 to 50 mg of N-hydroxy-3-[4-[[[2-(2-methyl-1H-indol-3-yl)ethyl]amino]methyl]phenyl]-2E-2-propenamide free base was suspended in 1 ml of a solvent as listed in Table 4. A stoichiometric amount of citric acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 4

| Solvent | T, ° C. | Physical Appear. | Crystallinity and Form | LOD, % $T_{decomposit}$ | $^1$H-NMR |
|---|---|---|---|---|---|
| IPA:H$_2$O (1:0.05) | 60 | SAM to FFP | excellent A | 0.4 184.3 | 3.98 (H$_{bz}$) |
| Acetone | ambient 60 | FFP to SAM to FFP | excellent A | 5.0 to 5.8 | — |

TABLE 4-continued

| Solvent | T, °C. | Physical Appear. | Crystallinity and Form | LOD, % $T_{decomposit}$ | $^1$H-NMR |
|---|---|---|---|---|---|
| EtOH | 60 | SAM to FFP | excellent A | — | — |
| IPA:H$_2$O (1:0.025) | 60 | SAM to FFP | excellent A | 0.3 181.0 | — |
| IPA:H$_2$O (1:0.05) | 60 | SAM to FFP | excellent A | — | — |
| Acetone:H$_2$O (1:0.025) | 60 | SAM to FFP | excellent A | — | — |
| Acetone:H$_2$O (1:0.05) | 60 | SAM to FFP | excellent A | 0.7 177.0 | — |

Heating to 60° C. (acetone and ethanol), as well as the introduction of water (isopropyl alcohol and water, acetone and water at 60° C.) yielded a highly crystalline salt that does not contain any solvent or water. A high LOD value for acetone at ambient/60° C. is due to the presence of amorphous material within the crystalline powder. The stoichiometry of the salt could not be determined by $^1$H-NMR in DMSO-d$_6$, since the expected peak for the citrate ion coincides with that of the solvent. However, $^{13}$C-NMR spectroscopy indicated the presence of two $^{13}$C=O signals at 177.3 and 171.6 ppm. The former is due to the protonated carboxylic group and the latter to the unprotonated carboxylate. Therefore, the salt stoichiometry is either 2:1 (most likely) or 1:1.

EXAMPLE 5

Formation of Hemi-Fumarate Salt

About 40 to 50 mg of N-hydroxy-3-[4-[[[2-(2-methyl-1H-indol-3-yl)ethyl]amino]methyl]phenyl]-2E-2-propenamide free base monohydrate was suspended in 1 ml of a solvent as listed in Table 5. A stoichiometric amount of fumaric acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 5

| Solvent | T, °C. | Physical Appear. | Crystallinity and Form | LOD, % $T_{decomposit.}$ | $^1$H-NMR |
|---|---|---|---|---|---|
| EtOH | ambient | FFP to SAM to FFP | excellent B | 1.1 + 1.7 (2-step) 213.2 | 3.93 (H$_{bz}$) 6.50 (1H, fumarate) |
| IPA | ambient | FFP | consists of one intense peak H$_A$ | 3.4 + 6.0 (2-step) 159.8 | 3.91 (H$_{bz}$) 6.50 (1H, fumarate) only small amount of IPA |
| EtOH:H$_2$O (1:0.05) | ambient | FFP to SAM to FFP | excellent A | 0.7 217.4 | 3.90 (H$_{bz}$) 6.49 (1H, fumarate) |
| IPA:H$_2$O (1:0.05) | ambient | FFP | excellent A | 1.5 208.2 | — |
| IPA:H$_2$O (1:0.05) | ambient | FFP | excellent A | — | — |
| EtOH:H$_2$O (1:0.025) | ambient | FFP to SAM to FFP | poor A | 0.7 154.8 | — |
| EtOH:H$_2$O (1:0.05) | ambient | FFP to SAM to FFP | excellent A | 0.9 217.1 | 3.90 (H$_{bz}$) 6.49 (1H, fumarate) |

The salt forming reaction in isopropyl alcohol and acetone at ambient temperature produced fumarate salts of stoichiometry 2:1 (protonated base:fumarate), i.e., hemi-fumarate salts. Although none of them was a solvate, they had poor crystallinity and a low decomposition temperature. The LOD for isopropyl alcohol at ambient temperature was most likely associated with the loss of water (most likely H$_A$ form). The salt forming reaction in ethanol, ethanol and water, and isopropyl alcohol and water, all at ambient temperature or 60° C., produced a fumarate salt of stoichiometry 2:1 (protonated base:fumarate)), i.e., hemi-fumarate salt. The salt forming reaction in ethanol and water and isopropyl alcohol and water (1:0.05), ambient or 60° C., produced identical XRPD spectra (anhydrous Form A). The spectrum of the salt formed by ethanol at ambient temperature, albeit similar, displays some small differences and it may represent a unique, hemi-fumarate polymorph (Form B) of similar structure.

EXAMPLE 6

Formation of Gentisate Salt

About 40 to 50 mg of N-hydroxy-3-[4-[[[2-(2-methyl-1H-indol-3-yl)ethyl]amino]methyl]phenyl]-2E-2-propenamide free base was suspended in 1 ml of a solvent as listed in Table 6. A stoichiometric amount of 2,5-dihydroxybenzoic acid (gentisic acid) was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 6

| Solvent | T, °C. | Physical Appear. | Crystallinity and Form | LOD, % $T_{decomposit.}$ | $^1$H-NMR |
|---|---|---|---|---|---|
| EtOH:H$_2$O (1:0.05) | 60 | Clear solut. to FFP | excellent A | 0.3 235.5 | 4.18 (H$_{bz}$) 6.61 (1H, gentisate) |

The gentisate salt prepared was highly crystalline, anhydrous, and decomposed at a very high temperature. The stoichiometry of the salt is 1:1 by NMR.

EXAMPLE 7

Formation of Monohydrate Lactate Salt

About 40 to 50 mg of N-hydroxy-3-[4-[[[2-(2-methyl-1H-indol-3-yl)ethyl]amino]methyl]phenyl]-2E-2-propenamide free base was suspended in 1 ml of a solvent as listed in Table 7. A stoichiometric amount of lactic acid was subsequently added to the suspension. The mixture was stirred at ambient temperature and when a clear solution formed, stirring continued at 4° C. Solids were collected by filtration and analyzed by XRPD, TGA and $^1$H-NMR.

TABLE 7

| Solvent | T, ° C. | Physical Appear. | Crystallinity and Form | LOD, % ($T_{desolvation}$) $T_{decomposit.}$ | $^1$H-NMR |
|---|---|---|---|---|---|
| IPA | 4 | FFP | excellent $H_A$ | 4.3 (79.3) 156.3 | — |
| Acetone | 4 | FFP | excellent $H_A$ | 4.5 (77.8) 149.5 | 4.18 ($H_{bz}$) |

The salt forming reaction in isopropyl alcohol and acetone at 4° C. produced a stoichiometric (1:1) lactate salt, a monohydrate. The salt is crystalline, begins to dehydrate above 77° C., and decomposes above 150° C.

EXAMPLE 8

Formation of Maleate Salt

About 40 to 50 mg of N-hydroxy-3-[4-[[[2-(2-methyl-1H-indol-3-yl)ethyl]amino]methyl]phenyl]-2E-2-propenamide free base monohydrate was suspended in 1 ml of a solvent as listed in Table 8. A stoichiometric amount of maleic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 8

| Solvent | T, ° C. | Physical Appear. | Crystallinity and Form | LOD, % $T_{decomposit.}$ | $^1$H-NMR |
|---|---|---|---|---|---|
| EtOH | RT to 4 | Clear solut. to FFP | Excellent $H_A$? | 6.2 (RT) 150 | 4.22 ($H_{bz}$) 6.01 (2H, maleate) |
| IPA | 60 | SAM to FFP | Excellent A | 0.2 178.1 | 4.22 ($H_{bz}$) 6.01 (2H, maleate) |
| Acetone | 60 | SAM to FFP | Excellent A | 0.2 176.1 | 4.22 ($H_{bz}$) 6.01 (2H, maleate) |

The salt forming reaction in isopropyl alcohol and acetone at 60° C. produced highly crystalline, anhydrous solids that decompose above 180° C. Maleic acid was the only dicarboxylic acid that produced a 1:1 salt with N-hydroxy-3-[4-[[[2-(2-methyl-1H-indol-3-yl)ethyl]amino]methyl]phenyl]-2E-2-propenamide. Its $^1$H-NMR spectrum displays a resonance at 6.01 ppm, corresponding to the two olefinic protons, and a resonance at 10.79 ppm due to one unprotonated carboxylic acid. Maleic acid also formed a salt with high water content that is lost under mild heating conditions. It is likely that the salt forming reaction in ethanol (RT to 4° C.) produced a hydrate (form $H_A$).

EXAMPLE 9

Formation of Hemi-Malate Salt

About 40 to 50 mg of N-hydroxy-3-[4-[[[2-(2-methyl-1H-indol-3-yl)ethyl]amino]methyl]phenyl]-2E-2-propenamide free base monohydrate was suspended in 1 ml of a solvent as listed in Table 9. A stoichiometric amount of malic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 9

| Solvent | T, ° C. | Physical Appear. | Crystallinity and Form | LOD, % $T_{decompos.}$ | $^1$H-NMR |
|---|---|---|---|---|---|
| EtOH:H$_2$O (1:0.05) | 60 | SAM to FFP | excellent A | 1.9 206.0 | 3.96 ($H_{bz}$) 3.83 (0.5H, malate) |
| EtOH | 60 | SAM to FFP | excellent A | 0.4 199.3 | — |
| IPA | 60 | SAM to FFP | excellent A | — | — |
| Acetone | 60 | SAM to FFP | excellent $S_A$ | 0.6 95 | 3.97 ($H_{bz}$) 3.84 (0.5H, malate) |
| EtOH:H$_2$O (1:0.05) | ambient | SAM to FFP | excellent A | — | — |

The salt forming reaction in ethanol and water, ethanol and isopropyl alcohol produced the same crystalline and anhydrous hemi-malate salt. The difference in LOD between ethanol and water (1:0.05) and ethanol may reflect varying amounts of amorphous material in the two samples. The salt forming reaction in acetone afforded a different hemi-malate salt that continuously loses weight above ~95° C. This salt is an acetone solvate (form $S_A$). Solvent loss and decomposition are closely spaced thermal events.

EXAMPLE 10

Formation of Hemi-Malonate Salt

About 40 to 50 mg of N-hydroxy-3-[4-[[[2-(2-methyl-1H-indol-3-yl)ethyl]amino]methyl]phenyl]-2E-2-propenamide free base was suspended in 1 ml of a solvent as listed in Table 10. A stoichiometric amount malonic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 10

| Solvent | T, ° C. | Physical Appear. | Crystallinity and Form | LOD, % $T_{decompos.}$ | $^1$H-NMR |
|---|---|---|---|---|---|
| EtOH | 60 | SAM to FFP | poor A | 1.0 169.5 | — |
| IPA | 60 | SAM to FFP | good A | 1.5 174.1 | 4.00 ($H_{bz}$) 2.69 (1H, malonate) |
| Acetone | 60 | SAM to FFP | good A | — | — |

TABLE 10-continued

| Solvent | T, °C. | Physical Appear. | Crystallinity and Form | LOD, % $T_{decompos.}$ | $^1$H-NMR |
|---|---|---|---|---|---|
| Acetone | ambient | FFP to SAM to FFP | good A | — | — |

All reactions afforded the same hemi-malonate salt. The crystallinity is usually good, although an amorphous halo could be seen in all the XRPD spectra. The water associated with these materials is likely due to increased moisture sorption by the amorphous component. Ambient conditions during synthesis appear to produce a better quality salt.

EXAMPLE 11

Formation of Mesylate Salt

About 40 to 50 mg of N-hydroxy-3-[4-[[[2-(2-methyl-1H-indol-3-yl)ethyl]amino]methyl]phenyl]-2E-2-propenamide free base monohydrate was suspended in 1 ml of a solvent as listed in Table 11. A stoichiometric amount of methanesulfonic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 11

| Solvent | T, °C. | Physical Appear. | Crystallinity and Form | LOD, % $T_{decompos.}$ | $^1$H-NMR |
|---|---|---|---|---|---|
| Acetone | 60 | SAM to FFP | Excellent A + B ? | 1.6 172.8 | 4.22 ($H_{bz}$) 2.33 (~5H, methane sulfonate) |
| AcOEt | ambient | FFP | Excellent A | 1.3 + 1.3 (2-step) 170.9 | 4.22 ($H_{bz}$) 2.36 (~5H, methane sulfonate) |

The salt forming reaction in ethyl acetate afforded a yellow salt, upon stirring at room temperature. The salt (form A) is crystalline, displays a 2-step weight loss and, by NMR, does not contain any solvent but appears to have more than one molecule of methanesulfonate (mesylate). The salt forming reaction in acetone afforded isolation of a white powder after heating at 60° C. It displayed excellent crystallinity but may be a composite of more than one polymorphic form (forms A and B). By NMR, it does not contain any solvent but appears to contain more than one molecule of methanesulfonate.

Another salt forming reaction in ethyl acetate, in which reaction is initiated at ambient temperature and then the obtained yellowish powder suspension is heated to 50° C., afforded isolation of a new form B, as shown in FIG. 5.

EXAMPLE 12

Formation of Oxalate Salt

About 40 to 50 mg of N-hydroxy-3-[4-[[[2-(2-methyl-1H-indol-3-yl)ethyl]amino]methyl]phenyl]-2E-2-propenamide free base was suspended in 1 ml of a solvent as listed in Table 12. A stoichiometric amount of salt forming agent oxalic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 12

| Solvent | T, °C. | Physical Appear. | Crystallinity and Form | LOD, % $T_{decompos.}$ | $^1$H-NMR |
|---|---|---|---|---|---|
| EtOH:H$_2$O (1:0.05) | 60 | FFP | Poor | — | — |
| IPA:H$_2$O (1:0.05) | 60 | FFP | Poor | — | — |
| EtOH | ambient | waxy solid | Amorphous | — | — |
| IPA | ambient | waxy solid | Amorphous | — | — |
| Acetone | ambient | waxy solid | Amorphous | — | — |

Oxalate salts, although precipitated immediately upon addition of oxalic acid to suspensions of N-hydroxy-3-[4-[[[2-(2-methyl-1H-indol-3-yl)ethyl]amino]methyl]phenyl]-2E-2-propenamide, were hard to isolate and appear to absorb water during filtration.

EXAMPLE 13

Formation of Phosphate Salt

About 40 to 50 mg of N-hydroxy-3-[4-[[[2-(2-methyl-1H-indol-3-yl)ethyl]amino]methyl]phenyl]-2E-2-propenamide free base monohydrate was suspended in 1 ml of a solvent as listed in Table 13. A stoichiometric amount of phosphoric acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 13

| Solvent | T/° C. | Physical Appear. | Crystallinity and Form | LOD % $T_{decompos.}$ | $^1$H-NMR |
|---|---|---|---|---|---|
| EtOH:H$_2$O (1:0.05) | 60 | FFP | excellent $H_A$ | 7.0 179.6 | 3.94 ($H_{bz}$) |
| EtOH | ambient | FFP | good $S_A$ | ~6.6 | 1.1 (~1.5 H, EtOH) 4.00 ($H_{bz}$) |
| IPA | ambient | FFP | excellent $S_B$ | ~7.0 | 1.02 (3-4 H, IPA) 4.00 ($H_{bz}$) |
| Acetone | RT to 60 | SAM to FFP | excellent A | 1.0 187.4 | 4.00 ($H_{bz}$) |
| AcOEt | RT to 60 | SAM to FFP | good A | 1.2 175.5 | — |

The salt forming reaction in ethanol and isopropyl alcohol gave ethanol and isopropanol hemi-solvates (forms $S_A$ and $S_B$, respectively). In ethanol and water, only traces of ethanol were detected by NMR, in spite of the large LOD. The material is either hygroscopic or a hydrate (form $H_A$) that loses water upon gentle heating and vacuum conditions (the loss of water measured by TGA is complete in by ~60° C. at 10° C./min). The salt forming reaction in acetone and ethyl acetate produced the same crystalline and anhydrous phosphate salt (form A). The stoichiometry is most likely 1:1. The salt displays a high decomposition temperature.

EXAMPLE 14

Formation of Propionate Salt

About 40 to 50 mg of N-hydroxy-3-[4-[[[2-(2-methyl-1H-indol-3-yl)ethyl]amino]methyl]phenyl]-2E-2-propenamide free base monohydrate was suspended in 1 ml of a solvent as listed in Table 14. A stoichiometric amount of propionic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 14

| Solvent | T, °C. | Physical Appear. | Crystallinity and Form | LOD, % $T_{decompos.}$ | $^1$H-NMR |
|---|---|---|---|---|---|
| IPA | 60 | FFP | excellent $S_A$ | 15.1 | 0.97 (3H, propionic) 1.02 (~4 H, IPA) 3.73 ($H_{bz}$) |
| Acetone | 60 | FFP | Excellent A | 7.0 98.9 | 0.97 (3H, propionic) 3.73 (Hbz) |
| AcOEt | 60 | FFP | Excellent A | 6.3 ~100 | — |

A salt forming reaction in ethanol afforded the unreacted free base (most likely form $H_B$). Isopropyl alcohol produced an IPA solvate of the propionate salt (form $S_A$). Based on NMR, the IPA content is ~0.5. The salt shows a weight loss of 15%, which corresponds to the loss of IPA plus an unidentified component. The salt forming reaction in acetone and ethyl acetate produced the same crystalline and unsolvated salt (form A). A weight loss of 6.3 to 7%, that starts at ~100° C., is due to water (if the salt is a hydrate), propionic acid or a decomposition product. Upon completion of weight loss (~140° C.), the salt decomposes. It should be pointed out that when the material is dissolved in DMSO for NMR, free propionic acid and only traces of propionate were detected.

EXAMPLE 15

Formation of Sulfate Salt

About 40 to 50 mg of N-hydroxy-3-[4-[[[2-(2-methyl-1H-indol-3-yl)ethyl]amino]methyl]phenyl]-2E-2-propenamide free base monohydrate was suspended in 1 ml of a solvent as listed in Table 15. A stoichiometric amount of sulfuric acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 15

| Solvent | T, °C. | Physical Appear. | Crystallinity and Form | LOD, % $T_{decompos.}$ | $^1$H-NMR |
|---|---|---|---|---|---|
| IPA | 60 | SAM to FFP | excellent $S_A$ | 8.9 to 12 162 | 1.02 (6H, IPA) 1.10 (3H, IPA$^+$) 4.22 ($H_{bz}$) |
| AcOEt | ambient | FFP | Poor A | ~6.7 ~160 | 4.22 ($H_{bz}$) |

The salt forming reaction in isopropyl alcohol afforded isolation of a white crystalline salt. It was identified as an isopropanol solvate (form $S_A$), containing 1.5 mol of IPA per formula unit. In DMSO, 0.5 mol of IPA is protonated. The salt forming reaction in ethyl acetate afforded isolation of a yellow hygroscopic powder (form A). During filtration, the sample visibly absorbed moisture, and its poor crystallinity is attributed to this effect.

EXAMPLE 16

Formation of Hemi-Succinate Salt

About 40 to 50 mg of N-hydroxy-3-[4-[[[2-(2-methyl-1H-indol-3-yl)ethyl]amino]methyl]phenyl]-2E-2-propenamide free base monohydrate was suspended in 1 ml of a solvent as listed in Table 16. A stoichiometric amount of succinic acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 16

| Solvent | T, °C. | Physical Appear. | Crystallinity and Form | LOD, % $T_{decompos.}$ | $^1$H-NMR |
|---|---|---|---|---|---|
| EtOH:H$_2$O (1:0.05) | 60 | SAM to FFP | Excellent A | 1.1 203.7 | 2.31 (2H, succinate) 3.86 ($H_{bz}$) |
| IPA:H$_2$O (1:0.05) | 60 | SAM to FFP | Excellent $H_A$ | 4.6 | 2.31 (2H, succinate) 3.85 ($H_{bz}$) |
| EtOH | ambient | FFP to SAM to FFP | Excellent A | 1.1 194.6 | 2.31 (2H, succinate) 3.85 ($H_{bz}$) |
| IPA | ambient | FFP | Good $S_A$ | 2.8 + 4.6 (90.6) (2-step) 155.8 | 1.02 (~3H, IPA) 2.32 (2H, succinate) 3.88 ($H_{bz}$) |
| Acetone | ambient | FFP | Good B | 1.5 + 1.3 (2-step) 162.3 | 2.31 (2H, succinate) 3.86 ($H_{bz}$) |

TABLE 16-continued

| Solvent | T, °C. | Physical Appear. | Crystallinity and Form | LOD, % $T_{decompos.}$ | $^1$H-NMR |
|---|---|---|---|---|---|
| AcOEt | ambient | FFP | Good B | 1.3 + 2.9 154.5 | — |
| EtOH | 60 | SAM to FFP | Excellent A | — | — |
| EtOH:H$_2$O (1:0.025) | 60 | SAM to FFP | Excellent A | 1.0 197.3 | 2.31 (2H, succinate) 3.85 (H$_{bz}$) |
| EtOH:H$_2$O (1:0.05) | 60 | SAM to FFP | Excellent A | — | — |

Four distinctly different hemi-succinate salts were isolated: a monohydrate (form A) (ethanol at ambient), a hemi-solvate of isopropanol (form S$_A$) (isopropyl alcohol), and two unsolvated forms A and B. Form A displays higher crystallinity, minimal weight loss up to 200° C., and higher decomposition temperature. In addition, it could be synthesized reproducibly, as demonstrated in ethanol and ethanol and water at 60° C.

EXAMPLE 17

Formation of Hemi-Tartarate Salt

About 40 to 50 mg of N-hydroxy-3-[4-[[[2-(2-methyl-1H-indol-3-yl)ethyl]amino]methyl]phenyl]-2E-2-propenamide free base monohydrate was suspended in 1 ml of a solvent as listed in Table 17. A stoichiometric amount of tartaric acid was subsequently added to the suspension. The mixture was stirred at either 60° C. or ambient temperature (where a clear solution formed, stirring continued at 4° C.). Solids were collected by filtration and analyzed by XRPD, TGA and in some instances $^1$H-NMR.

TABLE 17

| Solvent | T/° C. | Physical Appear. | Crystallinity and Form | LOD % $T_{decompos.}$ | $^1$H-NMR |
|---|---|---|---|---|---|
| EtOH:H$_2$O (1:0.05) | RT to 60 | FFP to SAM to FFP | Excellent A | 0.5 206.9 | 3.86 (1H, tartarate) 3.95 (H$_{bz}$) |
| EtOH:H$_2$O (1:0.025) | 60 | SAM to FFP | Excellent A | — | — |
| EtOH:H$_2$O (1:0.05) | 60 | SAM to FFP | Excellent A | 0.5 207.6 | 3.86 (1H, tartarate) 3.95 (H$_{bz}$) |
| EtOH | 60 | SAM to FFP | Excellent A | — | — |
| IPA:H$_2$O (1:0.05 | 60 | SAM to FFP | Good B | 1.9 and 3.4 >160° C. | 3.90 (1H, tartarate) 3.96 (H$_{bz}$) |

The salt forming reaction of the free base with tartaric acid required heating to elevated temperatures. A highly crystalline anhydrous salt that decomposed above 200° C. was isolated as a hemi-tartarate and was labeled as form A. Form B was isolated once in isopropyl alcohol and water at 60° C. and, although very similar in structure with A, significant differences were seen in its XRPD pattern.

EXAMPLE 18

Formation of Anhydrous Lactate Salt

DL-lactic acid (4.0 g, 85% solution in water, corresponding to 3.4 g pure DL-lactic acid) is diluted with water (27.2 g), and the solution is heated to 90° C. (inner temperature) for 15 hours. The solution is allowed to cool down to room temperature and is used as lactic acid solution for the following salt formation step.

N-hydroxy-3-[4-[[[2-(2-methyl-1H-indol-3-yl)ethyl]amino]methyl]phenyl]-2E-2-propenamide free base (10.0 g) is placed in a 4-necked reaction flask with mechanical stirrer. Demineralized water (110.5 g) is added, and the suspension is heated to 65° C. (inner temperature) within 30 minutes. The DL-lactic acid solution is added to this suspension during 30 min at 65° C. During the addition of the lactate salt solution, the suspension converted into a solution. The addition funnel is rinsed with demineralized water (9.1 g), and the solution is stirred at 65° C. for an additional 30 minutes. The solution is cooled down to 45° C. (inner temperature) and seed crystals (10 mg N-hydroxy-3-[4-[[[2-(2-methyl-1H-indol-3-yl)ethyl]amino]methyl]phenyl]-2E-2-propenamide lactate monohydrate) are added at this temperature. The suspension is cooled down to 33° C. and is stirred for additional 20 hours at this temperature. The suspension is re-heated to 65° C., stirred for 1 hour at this temperature and is cooled to 33° C. within 1 hour. After additional stirring for 3 hours at 33° C., the product is isolated by filtration, and the filter cake is washed with demineralized water (2×20 g). The wet filter-cake is dried in vacuo at 50° C. to obtain the anhydrous N-hydroxy-3-[4-[[[2-(2-methyl-1H-indol-3-yl)ethyl]amino]methyl]phenyl]-2E-2-propenamide lactate salt as a crystalline product. The product is identical to the monohydrate salt (form H$_A$) in HPLC and in 1H-NMR, with the exception of the integrals of water signals in the 1H-NMR spectra.

In additional salt formation experiments carried out according to the procedure described above, the product solution was filtered at 65° C. before cooling to 45° C., seeding and crystallization. In all cases, form A (anhydrate form) was obtained as product.

EXAMPLE 19

Formation of Anhydrous Lactate Salt

DL-lactic acid (2.0 g, 85% solution in water, corresponding to 1.7 g pure DL-lactic acid) is diluted with water (13.6 g), and the solution is heated to 90° C. (inner temperature) for 15 hours. The solution was allowed to cool down to room temperature and is used as lactic acid solution for the following salt formation step.

N-hydroxy-3-[4-[[[2-(2-methyl-1H-indol-3-yl)ethyl]amino]methyl]phenyl]-2E-2-propenamide free base (5.0 g) is placed in a 4-necked reaction flask with mechanical stirrer. Demineralized water (54.85 g) is added, and the suspension is heated to 48° C. (inner temperature) within 30 minutes. The DL-lactic acid solution is added to this suspension during 30 minutes at 48° C. A solution is formed. Seed crystals are added (as a suspension of 5 mg N-hydroxy-3-[4-[[[2-(2-methyl-1H-indol-3-yl)ethyl]amino]methyl]phenyl]-2E-2-propenamide lactate salt, anhydrate form A, in 0.25 g of water) and stirring is continued for 2 additional hours at 48° C. The temperature is raised to 65° C. (inner temperature) within 30 minutes, and the suspension is stirred for additional 2.5 hours at this temperature. Then the temperature is cooled down to 48° C. within 2 hours, and stirring is continued at this temperature for additional 22 hours. The product is isolated by filtration and the filter cake is washed with demineralized water (2×10 g). The wet filter-cake is dried in vacuo at 50° C. to obtain anhydrous N-hydroxy-3-[4-[[[2-(2-methyl-1H-indol-3-yl)ethyl]amino]methyl]phenyl]-2E-2-propenamide lactate salt (form A) as a crystalline product.

EXAMPLE 20

Conversion of Monohydrate Lactate Salt to Anhydrous Lactate Salt

DL-lactic acid (0.59 g, 85% solution in water, corresponding to 0.5 g pure DL-lactic acid) is diluted with water (4.1 g), and the solution is heated to 90° C. (inner temperature) for 15 hours. The solution is allowed to cool down to room temperature and is used as lactic acid solution for the following salt formation step.

10 g of N-hydroxy-3-[4-[[[2-(2-methyl-1H-indol-3-yl) ethyl]amino]methyl]phenyl]-2E-2-propenamide lactate salt monohydrate is placed in a 4-necked reaction flask. Water (110.9 g) is added, followed by the addition of the lactic acid solution. The addition funnel of the lactic acid is rinsed with water (15.65 g). The suspension is heated to 82° C. (inner temperature) to obtain a solution. The solution is stirred for 15 minutes at 82° C. and is hot filtered into another reaction flask to obtain a clear solution. The temperature is cooled down to 50° C., and seed crystals are added (as a suspension of 10 mg N-hydroxy-3-[4-[[[2-(2-methyl-1H-indol-3-yl)ethyl]amino] methyl]phenyl]-2E-2-propenamide lactate salt, anhydrate form, in 0.5 g of water). The temperature is cooled down to 33° C. and stirring is continued for additional 19 hours at this temperature. The formed suspension is heated again to 65° C. (inner temperature) within 45 minutes, stirred at 65° C. for 1 hour and cooled down to 33° C. within 1 hour. After stirring at 33° C. for additional 3 hours, the product is isolated by filtration and the wet filter cake is washed with water (50 g). The product is dried in vacuo at 50° C. to obtain crystalline anhydrous N-hydroxy-3-[4-[[[2-(2-methyl-1H-indol-3-yl) ethyl]amino]methyl]phenyl]-2E-2-propenamide lactate salt (form A).

EXAMPLE 21

Formation of Anhydrous Lactate Salt

DL-lactic acid (8.0 g, 85% solution in water, corresponding to 6.8 g pure DL-lactic acid) was diluted with water (54.4 g), and the solution was heated to 90° C. (inner temperature) for 15 hours. The solution was allowed to cool down to room temperature and was used as lactic acid solution for the following salt formation step.

N-hydroxy-3-[4-[[[2-(2-methyl-1H-indol-3-yl)ethyl] amino]methyl]phenyl]-2E-2-propenamide (20 g) is placed in a 1 L glass reactor, and ethanol/water (209.4 g of a 1:1 w/w mixture) is added. The light yellow suspension is heated to 60° C. (inner temperature) within 30 minutes, and the lactic acid solution is added during 30 minutes at this temperature. The addition funnel is rinsed with water (10 g). The solution is cooled to 38° C. within 2 hours, and seed crystals (20 mg of N-hydroxy-3-[4-[[[2-(2-methyl-1H-indol-3-yl)ethyl]amino] methyl]phenyl]-2E-2-propenamide lactate salt, anhydrate form) are added at 38° C. After stirring at 38° C. for additional 2 hours, the mixture is cooled down to 25° C. within 6 hours. Cooling is continued from 25° C. to 10° C. within 5 hours, from 10° C. to 5° C. within 4 hours and from 5° C. to 2° C. within 1 hour. The suspension is stirred for additional 2 hours at 2° C., and the product is isolated by filtration. The wet filter cake is washed with water (2×30 g), and the product is dried in vacuo at 45° C. to obtain crystalline anhydrous N-hydroxy-3-[4-[[[2-(2-methyl-1H-indol-3-yl)ethyl]amino]methyl] phenyl]-2E-2-propenamide lactate salt (form A).

EXAMPLE 22

Formation of Sodium Salt

About 50 mg of N-hydroxy-3-[4-[[[2-(2-methyl-1H-indol-3-yl)ethyl]amino]methyl]phenyl]-2E-2-propenamide free base monohydrate was suspended in 1 ml of methanol. A stoichiometric amount of sodium hydroxide was subsequently added to the suspension. The mixture was stirred at 50° C. Once a clear solution formed, stirring continued at 4° C. Solids were collected by filtration and analyzed by XRPD and TGA. The sodium salt of N-hydroxy-3-[4-[[[2-(2-methyl-1H-indol-3-yl) ethyl]amino]methyl]phenyl]-2E-2-propenamide was isolated as a yellow highly hygroscopic powder, which absorbed moisture during filtration.

EXAMPLE 23

Formation of Potassium Salt

About 50 mg of N-hydroxy-3-[4-[[[2-(2-methyl-1H-indol-3-yl)ethyl]amino]methyl]phenyl]-2E-2-propenamide free base monohydrate was suspended in 1 ml of methanol. A stoichiometric amount of potassium hydroxide was subsequently added to the suspension. The mixture was stirred at 50° C. Once a clear solution formed, stirring continued at 4° C. Solids were collected by filtration and analyzed by XRPD and TGA. The potassium salt of N-hydroxy-3-[4-[[[2-(2-methyl-1H-indol-3-yl)ethyl]amino]methyl]phenyl]-2E-2-propenamide was isolated as a yellow highly hygroscopic powder, which absorbed moisture during filtration.

EXAMPLE 24

Formation of Calcium Salt

About 50 mg of N-hydroxy-3-[4-[[[2-(2-methyl-1H-indol-3-yl)ethyl]amino]methyl]phenyl]-2E-2-propenamide free base monohydrate was suspended in 1 ml of methanol. A stoichiometric amount of sodium hydroxide was subsequently added to the suspension. The mixture was stirred at 50° C. Once a clear solution formed, a stoichiometric amount of calcium dichloride was added causing an immediate precipitation of yellowish solid. Solids were collected by filtration and analyzed by XRPD and TGA. The calcium salt of N-hydroxy-3-[4-[[[2-(2-methyl-1H-indol-3-yl)ethyl]amino] methyl]phenyl]-2E-2-propenamide was less hygroscopic than the sodium or potassium salt of N-hydroxy-3-[4-[[[2-(2-methyl-1H-indol-3-yl)ethyl]amino]methyl]phenyl]-2E-2-propenamide and could be readily isolated.

EXAMPLE 25

Formation of Zinc Salt

About 50 mg of N-hydroxy-3-[4-[[[2-(2-methyl-1H-indol-3-yl)ethyl]amino]methyl]phenyl]-2E-2-propenamide free base monohydrate was suspended in 1 ml of methanol. A stoichiometric amount of sodium hydroxide was subsequently added to the suspension. The mixture was stirred at 50° C. Once a clear solution formed, a stoichiometric amount of zinc sulfate was added causing an immediate precipitation of yellowish solid. Solids were collected by filtration and analyzed by XRPD and TGA. The zinc salt of N-hydroxy-3-[4-[[[2-(2-methyl-1H-indol-3-yl) ethyl]amino]methyl]phenyl]-2E-2-propenamide was less hygroscopic than the sodium or potassium salt of N-hydroxy-3-[4-[[[2-(2-methyl-1H-indol-3-yl) ethyl]amino]methyl]phenyl]-2E-2-propenamide and could be readily isolated.

EXAMPLE 26

Formation of Hydrochloride Salt 3.67 g (10 mmol) of the free base monohydrate (N-hydroxy-3-[4-[[[2-(2-methyl-1H-indol-3-yl) ethyl]amino]methyl]phenyl]-2E-2-propenamide) and 40 ml of absolute ethanol were charged in a 250 ml 3-neck flask equipped with a magnetic stirrer and an addition funnel. To the stirred suspension were added dropwise 7.5 ml of 2 M HCl (15 mmol, 50% excess), affording a clear solution. A white solid precipitated out within 10 minutes, and stirring continued at ambient for an additional 2 hours. The mixture was cooled in an ice bath for approximately 30 min, and the white solid was recovered by filtration. It was washed once with cold ethanol (10 ml) and dried overnight under vacuum to yield 3.72 g of the chloride salt of N-hydroxy-3-[4-[[[2-(2-methyl-1H-indol-3-yl)ethyl]amino]methyl]phenyl]-2E-2-propenamide (96.2%).

It should be noted that HCl was used in excess to improve the yield, although equimolar amounts afforded yields of greater than 80%. Di-salt formation via protonation of the methyl-1H-indol-3-yl ring does not occur even when HCl is used in large excess. Reactions with 1, 1.5, and 2 equivalents of HCl afforded the same monochloride salt as a product. In addition, NMR data show no shifts for any of the protons in the vicinity of the ring, as it would have happened upon protonation.

EXAMPLE 27

Formation of L-Tartarate Salt 3.67 g (10 mmol) of the free base monohydrate (N-hydroxy-3-[4-[[[2-(2-methyl-1H-indol-3-yl) ethyl]amino]methyl]phenyl]-2E-2-propenamide) and 50 ml of absolute ethanol were charged in a 250 ml 3-neck flask equipped with a magnetic stirrer and an addition funnel. The mixture was heated to 60° C., and to the hot suspension were added dropwise 0.83 g (5.5 mmol, 10% excess) of l-tartaric acid dissolved in 15 ml absolute ethanol. Initially, large yellow agglomerates formed that prevented adequate stirring, but overtime these were converted to free flowing and stirrable yellow powder. Stirring continued at 60° C. for 2 hours. The mixture was subsequently cooled to room temperature and placed in an ice bath for approximately 30 min. The yellow powder was recovered by filtration and washed once by cold absolute ethanol (10 ml). It was dried overnight under vacuum to yield 4.1 g of the l-tartarate (hemi-tartarate) salt of N-hydroxy-3-[4-[[[2-(2-methyl-1H-indol-3-yl)ethyl]amino]methyl]phenyl]-2E-2-propenamide (96.6%).

EXAMPLE 28

Formation of Lactate Monohydrate Salt 3.67 g (10 mmol) of the free base monohydrate (N-hydroxy-3-[4-[[[2-(2-methyl-1H-indol-3-yl) ethyl]amino]methyl]phenyl]-2E-2-propenamide) and 75 ml of acetone were charged in a 250 ml 3-neck flask equipped with a magnetic stirrer and an addition funnel. To the stirred suspension were added dropwise 10 ml of 1 M lactic acid in water (10 mmol) dissolved in 20 ml acetone, affording a clear solution. Stirring continued at ambient and a white solid precipitated out after approximately 1 hour. The mixture was cooled in an ice bath and stirred for an additional hour. The white solid was recovered by filtration and washed once with cold acetone (15 ml). It was subsequently dried under vacuum to yield 3.94 g of the lactate monohydrate salt of N-hydroxy-3-[4-[[[2-(2-methyl-1H-indol-3-yl)ethyl]amino]methyl]phenyl]-2E-2-propenamide (86.2%).

EXAMPLE 29

Formation of Mesylate Salt 3.67 g (10 mmol) of the free base monohydrate (N-hydroxy-3-[4-[[[2-(2-methyl-1H-indol-3-yl) ethyl]amino]methyl]phenyl]-2E-2-propenamide) and 75 ml of ethyl acetate were charged in a 250 ml 3-neck flask equipped with a mechanical stirrer and an addition funnel. To the stirred suspension were added dropwise 0.65 ml (10 mmol) of methane sulfonic acid dissolved in 20 ml of ethyl acetate, affording a stirrable suspension of a free flowing yellow powder. The mixture was heated to 50° C. and kept there overnight, and during that time the yellow powder converted to a white solid. The suspension was cooled to room temperature and the white solid was recovered by filtration. It was washed once with cold ethyl acetate (15 ml) and dried overnight under vacuum to yield 4.38 g of the mesylate salt of N-hydroxy-3-[4-[[[2-(2-methyl-1H-indol-3-yl)ethyl]amino]methyl]phenyl]-2E-2-propenamide (98.3%).

It is noted that the initially formed yellow powder is a polymorph of the mesylate salt that contains more than the equimolar amount of methane sulfonic acid. As a result, this solid is very highly hygroscopic. Upon gentle heating to 40 or 50° C. and within 2 to 4 hours, the yellow powder converts to a white crystalline solid that contains the equimolar amount of the methane sulfonic acid. This salt is non-hygroscopic. It is also advised that addition of the methane sulfonic acid is done at ambient temperature and the temperature increased afterwards. It was observed that addition at higher temperature afforded the immediate precipitation of the salt as a soft and gummy material.

EXAMPLE 30

Formation of Maleate Salt 3.67 g (10 mmol) of the free base monohydrate (N-hydroxy-3-[4-[[[2-(2-methyl-1H-indol-3-yl) ethyl]amino]methyl]phenyl]-2E-2-propenamide) and 75 ml of acetone were charged in a 250 ml 3-neck flask equipped with a mechanical stirrer and an addition funnel. The mixture was heated to 45° C., and to the hot suspension were added dropwise 1.16 g (10 mmol) of maleic acid dissolved in 25 ml acetone. Although the addition was slow, the salt precipitated out as a soft gummy solid hindering stirring. Stirring continued overnight at 45° C. and during that time the solid converted to a white free-flowing powder. The mixture was cooled to room temperature and placed in an ice bath for approximately 30 min. The white solid was recovered by filtration, washed once with cold acetone (15 ml), and dried overnight under vacuum to yield 4.21 g of the maleate salt of N-hydroxy-3-[4-[[[2-(2-methyl-1H-indol-3-yl)ethyl]amino]methyl]phenyl]-2E-2-propenamide (90.5%).

It is noted that a more preferable solvent for synthesis is 2-propanol. During optimization, however, it was observed that, in addition to the desired form, another polymorph with a low decomposition temperature (118.9° C.) could be isolated from 2-propanol as a yellow powder.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

EXAMPLE 31

Formation of the Lactate Salt

A flow diagram for the synthesis of LBH589 lactate is provided in FIG. A. A nomenclature reference index of the intermediates is provided below in the Nomenclature Reference Index:

| Nomenclature reference index | |
|---|---|
| Compound | Chemical name |
| 1 | 4-Bromo-benzaldehyde |
| 2 | Methyl acrylate |
| 3 | (2E)-3-(formylphenyl)-2-propenoic acid, methyl ester |
| 4 | 3-[4-[[[2-(2-Methyl-1H-indol-3-yl)ethyl]amino]methyl]phenyl]-2-propenoic acid, methyl ester, monohydrochloride |
| 5 | (2E)-N-hydroxy-3-[4-[[[2-(2-methyl-1H-indol-3-yl)ethyl]amino]methyl]phenyl]-2-propenamide |
| 6 | 2-hydroxypropanoic acid, compd. with 2(E)-N-hydroxy-3-[4-[[[2-(2-methyl-1H-indol-3-yl)ethyl]amino]methyl]phenyl]-2-propenamide |
| Z3a | 2-Methyl-1H-indole-3-ethanamine |
| Z3b | 5-Chloro-2-pentanone |
| Z3c | Phenylhydrazine |

Figure A: Synthesis of LBH589 Lactate

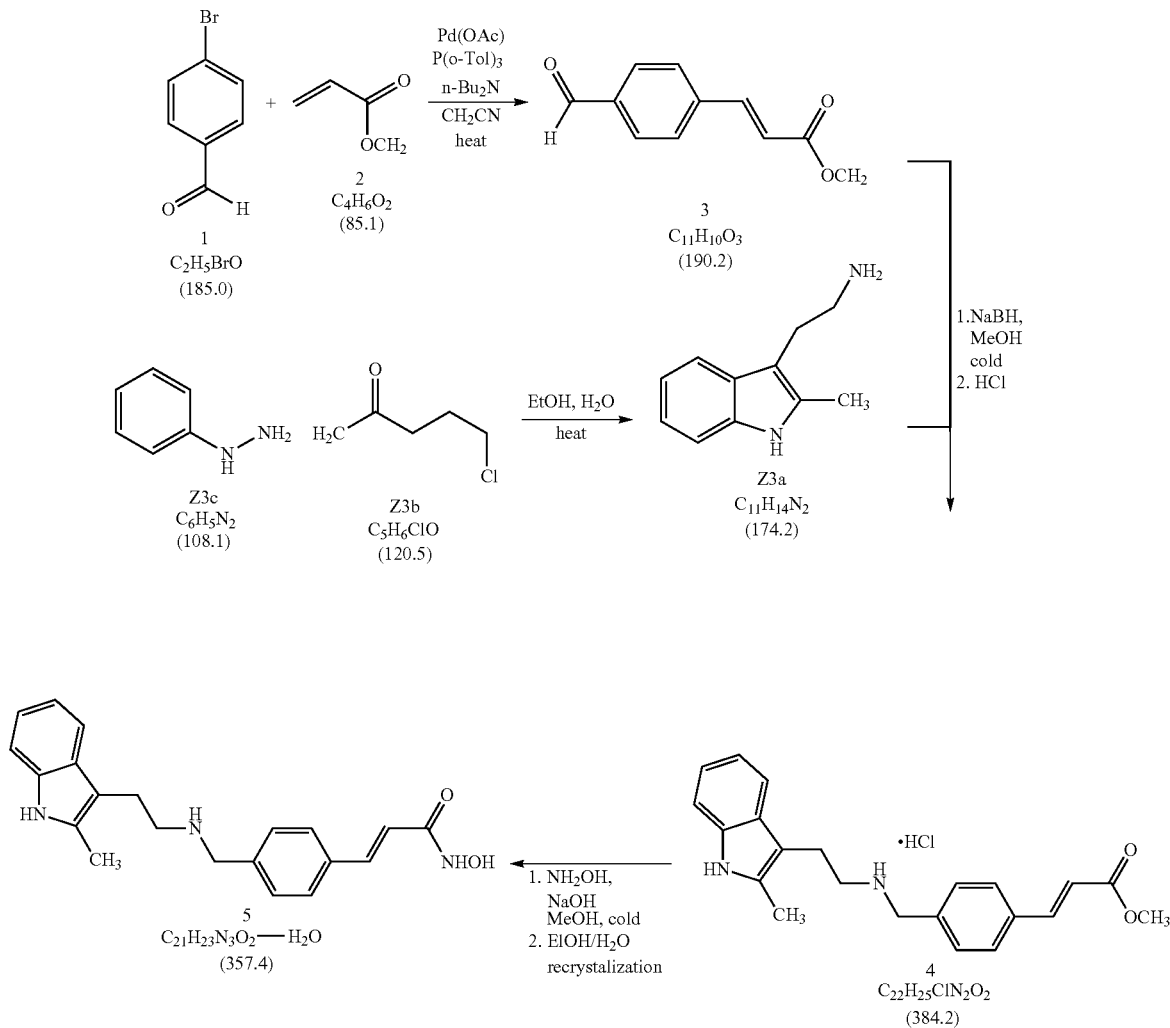

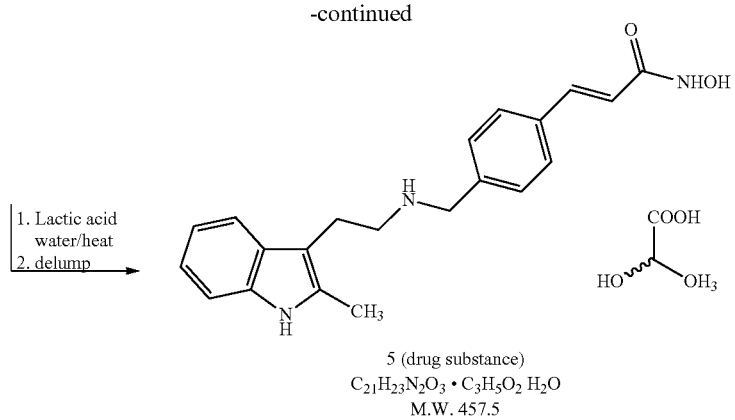

5 (drug substance)
C21H23N2O3 · C3H5O2 H2O
M.W. 457.5

The manufacture of LBH589 lactate (6) drug substance is via a convergent synthesis; the point of convergence is the condensation of indole-amine Z3a with aldehyde 3.

The synthesis of indole-amine Z3a involves reaction of 5-chloro-2 pentanone (Z3b) with phenylhydrazine (Z3c) in ethanol at reflux (variation of Fischer indole synthesis).

Product isolation is by an extractive work-up followed by crystallization. Preparation of aldehyde 3 is by palladium catalyzed vinylation (Heck-type reaction; Pd(OAc)2/P(o-Tol)3/Bu3N in refluxing CH3CN) of 4-bromo-benzylaldehyde (1) with methyl acrylate (2) with product isolation via precipitation from dilute HCl solution. Intermediates Z3a and 3 are then condensed to an imine intermediate, which is reduced using sodium borohydride in methanol below 0° C. (reductive amination). The product indole-ester 4, isolated by precipitation from dilute HCl, is recrystallized from methanol/water, if necessary. The indole ester 4 is converted to crude LBH589 free base 5 via reaction with hydroxylamine and sodium hydroxide in water/methanol below 0° C. The crude LBH589 free base 5 is then purified by recrystallization from hot ethanol/water, if necessary. LBH589 free base 5 is treated with 85% aqueous racemic lactic acid and water at ambient temperature. After seeding, the mixture is heated to approximately 65° C., stirred at this temperature and slowly cooled to 45-50° C. The resulting slurry is filtered and washed with water and dried to afford LBH589 lactate (6).

If necessary the LBH589 lactate 6 may be recrystallised once again from water in the presence of 30 mol % racemic lactic acid. Finally the LBH589 lactate is delumped to give the drug substance. If a rework of the LBH589 lactate drug substance 6 is required, the LBH589 lactate salt is treated with sodium hydroxide in ethanol/water to liberate the LBH589 free base 5 followed by lactate salt formation and delumping as described above.

All starting materials, reagents and solvents used in the synthesis of LBH589 lactate are tested according to internal specifications or are purchased from established suppliers against a certificate of analysis.

What is claimed is:

1. A method of preparing the lactate monohydrate salt of N-hydroxy-3-[4-[[[2-(2-methyl-1H-indol-3-yl)ethyl]amino]methyl]phenyl]-2E-2-propenamide comprising the steps of:
   (a) suspending N-hydroxy-3-[4-[[[2-(2-methyl-1H-indol-3-yl)ethyl]amino]methyl]phenyl]-2E-2-propenamide free base monohydrate in acetone;
   (b) adding lactic acid dropwise with stirring at ambient temperature, wherein the lactic acid is present in an equimolar amount;
   (c) stirring the reaction mixture for a time sufficient to cause precipitation of the lactate monohydrate salt; and
   (d) cooling the reaction mixture.

2. The method of claim 1 further comprising the steps of:
   (e) isolating the precipitated lactate monohydrate salt of N-hydroxy-3-[4-[[[2-indol-3-yl)ethyl]amino]methyl]phenyl]-2E-2-propenamide;
   (f) washing the salt with cold acetone; and
   (g) drying the salt.

3. A method of preparing the anhydrous lactate salt of N-hydroxy-3-[4-[[[2-(2-methyl-1H-indol-3-yl)ethyl]amino]methyl]phenyl]-2E-2-propenamide comprising the steps of:
   (a) providing a solution of lactic acid;
   (b) suspending N-hydroxy-3-[4-[[[2-(2-methyl-1H-indol-3-yl)ethyl]amino]methyl]phenyl]-2E-2-propenamide free base in water;
   (c) heating the suspension to an appropriate temperature;
   (d) adding the solution of lactic acid to form a solution;
   (e) seeding the solution with a suspension of the anhydrous lactate salt of N-hydroxy-3-[4-[[[2-(2-methyl-1H-indol-3-yl)ethyl]amino]methyl]phenyl]-2E-2-propenamide;
   (f) stirring the solution for a time;
   (g) heating the solution to a second appropriate temperature;
   (h) stirring the solution for a time;
   (i) cooling the solution; and
   (j) stirring the solution for a time sufficient to precipitate the anhydrous lactate salt of N-hydroxy-3-[4-[[[2-(2-methyl-1H-indol-3-yl)ethyl]amino]methyl]phenyl]-2E-2-propenamide.

4. The method of claim 3 further comprising the steps of:
   (k) isolating the precipitated anhydrous lactate salt of N-hydroxy-3-[4-[[[2-(2-methyl-1H-indol-3-yl)ethyl]amino]methyl]phenyl]-2E-2-propenamide;
   (l) washing the salt with water; and
   (m) drying the salt.

5. A method of preparing the anhydrous lactate salt of N-hydroxy-3-[4-[[[2-(2-methyl-1H-indol-3-yl)ethyl]amino]methyl]phenyl]-2E-2-propenamide comprising the steps of:
   (a) providing a solution of lactic acid;
   (b) suspending N-hydroxy-3-[4-[[[2-(2-methyl-1H-indol-3-yl)ethyl]amino]methyl]phenyl]-2E-2-propenamide free base in a 1:1 mixture of ethanol and water;
   (c) heating the suspension to an appropriate temperature;
   (d) adding the solution of lactic acid to form a solution;
   (e) cooling the solution;

(f) seeding the solution with anhydrous lactate salt of N-hydroxy-3-[4-[[[2-(2-methyl-1H-indol-3-yl)ethyl]amino]methyl]phenyl]-2E-2-propenamide;
(g) stirring the solution for a time;
(h) cooling the solution; and
(i) stirring the solution for a time sufficient to precipitate the anhydrous lactate salt of N-hydroxy-3-[4-[[[2-(2-methyl-1H-indol-3-yl)ethyl]amino]methyl]phenyl]-2E-2-propenamide.

6. The method of claim 5 further comprising the steps of:
(j) isolating the precipitated anhydrous lactate salt of N-hydroxy-3-[4-[[[2-(2-methyl-1H-indol-3-yl)ethyl]amino]methyl]phenyl]-2E-2-propenamide;
(k) washing the salt with water; and
(l) drying the salt.

* * * * *